United States Patent [19]

Badger

[11] Patent Number: 6,051,596
[45] Date of Patent: *Apr. 18, 2000

[54] IMMUNOSUPPRESSIVE COMPOSITIONS

[75] Inventor: Alison Mary Badger, Bryn Mawr, Pa.

[73] Assignee: AnorMED, Inc., Langley, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 08/904,932

[22] Filed: Aug. 1, 1997

Related U.S. Application Data

[63] Continuation of application No. 08/415,875, Apr. 3, 1995, abandoned, which is a continuation-in-part of application No. 08/179,462, Jan. 10, 1994, abandoned, which is a continuation of application No. 07/565,826, Aug. 10, 1990, abandoned.

[51] Int. Cl.$^7$ .......................... A01N 43/38; A01N 43/42; A61K 38/00
[52] U.S. Cl. ................ 514/409; 514/11; 514/278
[58] Field of Search .................. 514/409, 11, 278

[56] References Cited

U.S. PATENT DOCUMENTS 4,963,557  10/1990  Badger et al. ..................... 514/278

OTHER PUBLICATIONS

Journal of Pharmacology and Experimental et al., Therapeutics, vol. 2 #1, Oct. 3 1985, DiMartino et al., "Antiarthritic and Immunoregulatory Activity of Spieogermanium" pp. 103–110.

Immunopharacology, vol. 10, 1985 Badger et al., "Generation of Suppressor Cells in Normal Rats by Treatment with Spirogermanium, A Novel Heterocyclic Anticancer Drug" pp.201–200.

Chemical Abstracts, vol. 110, No 69098V, issued Feb.27, 1989. Yoshimura et al., "Effect of the new immunosuppressive agent FK 506 on lymphokine production and responsiveness of human peripheral blood lymphocytes", See page 26, Column 4, abstract 690980 Igaku no Ayumi 1988, vol. 147 (a), 783–4 (Japan).

Chemical Abstracts, vol. 87, No. 15, issued Oct. 10, 1977, Martel et al., "Inhibition of the immune response by rapamycin, a new antifungal antibiotic", See p. 90, Column 1,abstract #111825p, Can. J. Physiol Pharmacol 1977, vol. 55 (1), vol. 55 (1) 48–51.

Chemical Abstracts, Col. 95, No. 21, issued Nov. 23, 1981, Bunjes et al., "Cyclosporin A mediates immunosuppression of primary cycotoxic T cell response by imparing the release of interleukin 1 and interleukin 2", p. 28, column 1 abstract #180735, Eur. J.Immunol. 1981, vol. 11 (8).

*Primary Examiner*—Russell Travers
*Attorney, Agent, or Firm*—Morrison & Foerster LLP

[57] ABSTRACT

A pharmaceutical composition containing a non-specific (NS) suppressor cell inducing compound and cyclosporin A and a pharmaceutically acceptable carrier or diluent, and method of inducing an immunosuppressive effect in a mammal, including a hyman, in need thereof which comprises administering an effective dose of a non-specific suppressor cell inducing compound and cyclosporin A to such mammal.

5 Claims, No Drawings

IMMUNOSUPPRESSIVE COMPOSITIONS

This is a continuation of application Ser. No. 08/415,875, filed on Apr. 3, 1995, which was abandoned upon the filing hereof which is a continuation-in-part of U.S. Ser. No. 08/179,462, filed Jan. 10, 1994 which is a continuation of U.S. Ser. No. 07/565,826, filed Aug. 10, 1990, now abandoned.

This invention relates to a pharmaceutical composition containing a non-specific suppressor cell inducing compound and cyclosporin A and a pharmaceutically acceptable carrier or diluent. This invention also relates to a method of inducing an immunosuppressive effect in a mammal, including a human, in need thereof which comprises administering an effective dose of a non-specific suppressor cell inducing compound and cyclosporin A to such mammal.

BACKGROUND OF THE INVENTION

Conventional drugs used in the treatment of autoimmune diseases and graft/transplantation rejection, such as cyclosporin A, corticosteroids, azathioprine, polyclonal antilymphocyte globulins and monoclonal T cell antibodies are somewhat effective in electing an immunosuppressive response. However, their highly toxicity profiles frequently limit their clinical benefit. Thus, the treatment of autoimmune diseases, graft/transplantation rejection and other maladies requiring immunosuppression with agents having low-toxicity profiles remains a major clinical problem.

The use of monoclonal anti-IL2 receptor antibodies in combination with cyclosporin A has been reported. See, Diamantstein, T, et al., (1986) Immunobiol. 1:391–399; Kupiec-Weglinski, J. W., et al., (1988) Transplant Proc 20:207–216 and Hancock, W. W., et al., (1990), Transplantation 49:416–421. The use of bromocriptine in combination with cyclosporin A (Carrier, M., et al., (1990), Ann. Thorac. Surg. 9:129–32) and thalidomide in combination with cyclosporin A (Tamura, F., et al., (1990) transplantation 49:20–25) has also been reported.

Non-specific suppressor cell inducing compounds are agents which induce the production of a population of natural suppressor cells which do not have the characteristics of mature T cells, B cells, macrophages or natural killer cells and are therefore of the null or non-specific phenotype. Natural suppressor cells are capable of inhibiting a variety of immune responses in vivo.

The immunosuppressive activity associated with total lymphoid irradiation (TLI) has been attributed to the generation of a population(s) of natural suppressor cells. See, Strober, S., (1984) Ann. Rev. Immun. 2:219 and Maier, T., et al., (1986), Immunol. Today 7:312. The use of TLI as part of a combination treatment with cyclosporine and either cyclophosphamide (See, Yamaguchi, Y., et al., (1990), Transplantation 49:13–17) or splenectomy (See, Miyamura, K., et al., (1988), Bone Barrow Transplantation 3:457–461) has been reported.

Classes of compounds known to induce NS suppressor cells include N-amino alkyl azaspirogermanium alkanes (See, e.g., Badger, A., et al., (1985), Immunopharm. 10:201 and DiMartino, M. J., et al., (1986), J. Pharm. Exp. Ther. 236:103) and N-amino alkyl azaspiro alkanes (See, e.g., Badger, A., et al., (1989), Int. J. Immunopharmac. 11:839–846 and European Patent Application Publication Number 0310321 A2).

It has now been discovered that combining a non-specific suppressor cell inducing compound with cyclosporin A increases immunosuppressive activity in vivo to an extent beyond which either compound achieves alone or would be expected to achieve when combined.

SUMMARY OF THE INVENTION

This invention relates to a pharmaceutical composition containing a non-specific suppressor cell inducing compound and cyclosporin A. This invention also relates to a method of inducing an immunosuppressive effect in a mammal, including a human, in need thereof which comprises administering an effective amount of a non-specific suppressor cell inducing compound and cyclosporin A to such mammal.

DETAILED DESCRIPTION OF THE INVENTION

By the term "cyclosporin A" as used herein is meant the cyclic polypeptide of the formula

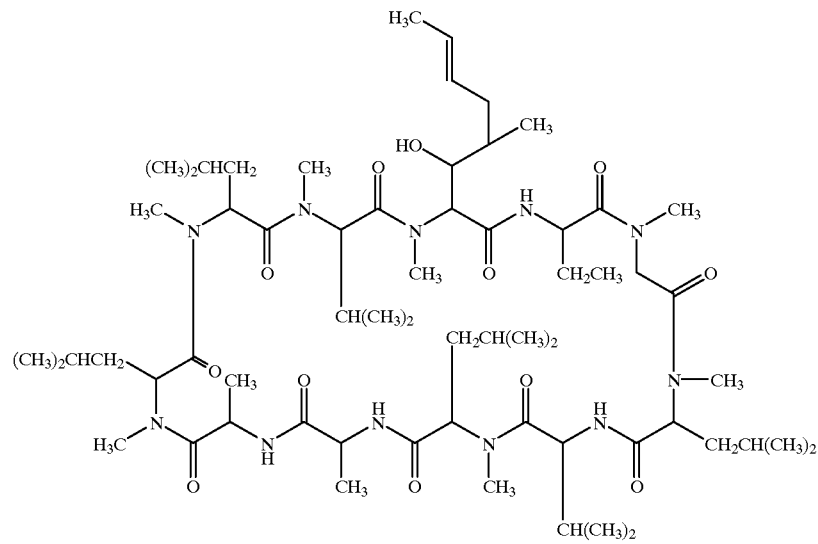

Cyclosporin A is produced as a metabolite by the fungus species *Tolypocladium inflatum Gams*. Chemically, cyclosporin A is designated as [R-[R,R-(E)]]-cyclic-(L-alanyl-D-alanyl-N-methyl-L-leucyl-N-methyl-L-leucyl-N-methyl-L-valyl-3-hydroxyN,4-dimethyl-L-2-amino-6-octenoyl-L-a-amino-butyryl-N-methylglycyl-N-methyl-L-leucyl-L-valyl-N-methyl-L-leucyl).

Cyclosporin A is commercially available in oral dosage form or intravenous dosage form under the trade name Sandimmune[R] and is manufactured by Sandoz Ltd., Basle Switzerland for Sandoz Pharmaceuticals Corporation, East Hanover, N.J. 07936. The total synthesis of cyclosporin A has been reported by Wenger, *Transplant Proc.* 15 (4), suppl. 1, 2230 (1983).

The non-specific suppressor cell inducing compounds for use in the composition and method of the invention are the N-aminoalkylazaspiro alkanes described in U.S. Pat. No. 4,963,557 to Badger, et al. issued on Oct. 16, 1990 the entire disclosure of which is hereby incorporated by reference, i.e., compounds of the formula (I):

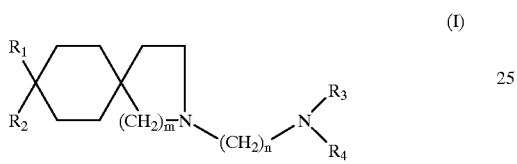

wherein:

n is 3–7;

m is 1 or 2;

$R_1$ and $R_2$ are the same or different and are selected from hydrogen or straight chain, branched chain or cyclic alkyl, provided that the total number of carbon atoms contained by $R_1$ and $R_2$ when taken together is 5–10; or $R_1$ and $R_2$ are joined together to form a cyclic alkyl group containing 3–7 carbon atoms;

$R_3$ and $R_4$ are the same or different and are selected from hydrogen or straight chain alkyl containing 1–3 carbon atoms; or $R_3$ and $R_4$ are joined together to form a cyclic alkyl group containing 4–7 carbon atoms;

or a pharmaceutically acceptable salt, hydrate or solvate thereof.

Preferred among the above formula (I) compounds are:

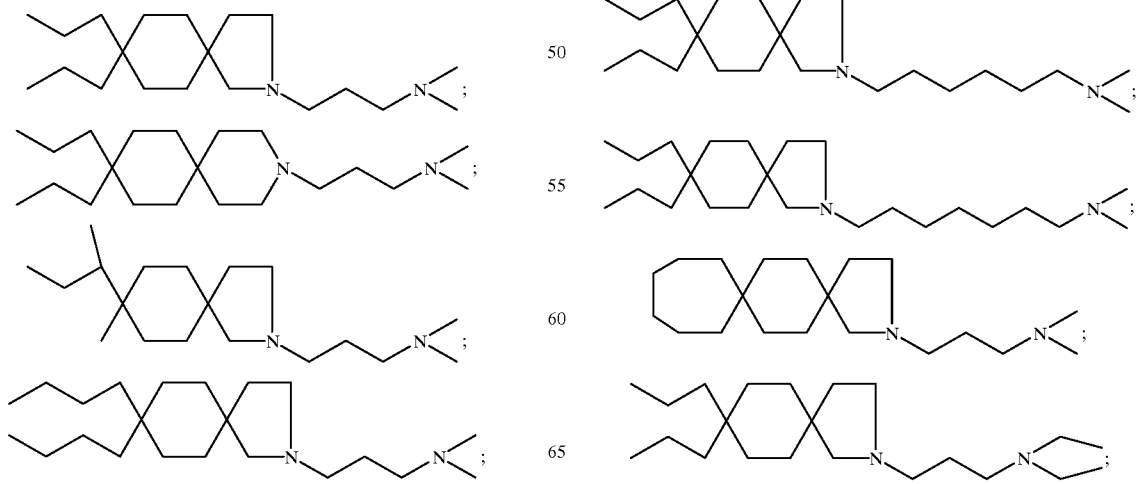

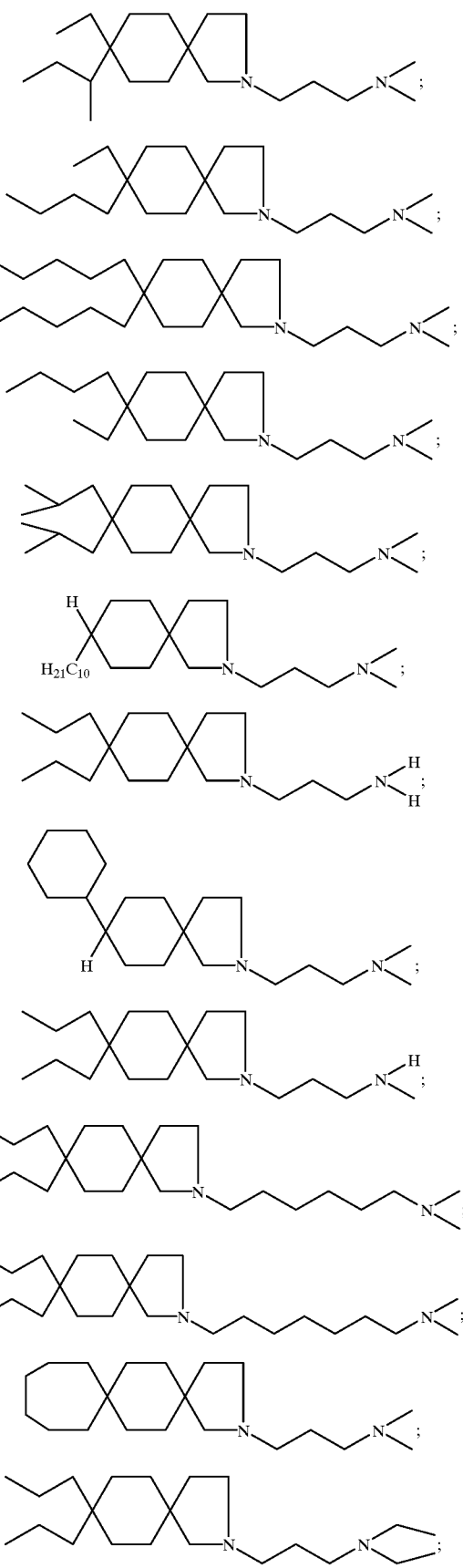

-continued or a salt thereof.

Especially preferred compound for use herein are:

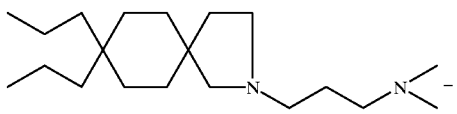

N,N-dimethyl-8,8-dipropyl-2-azaspiro[4,5]-decane-2-propanamine, (hereinafter referred to as 'Compound A');

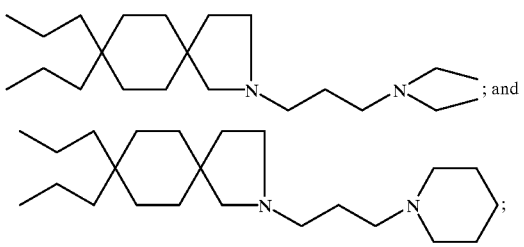

By the term "administering" an effective amount of a non-specific suppressor cell inducing compound and Cyclosporin A as used herein is meant either simultaneous administration or any manner of consecutive administration, i.e., either Cyclosporin A or the non-specific suppressor cell inducing compound may be administered first. Preferably, if the administration is not simultaneous, the two compounds are administered in a close time proximity to each other. Furthermore, it does not matter if the compounds are both administered in the same dosage form, e.g., Cyclosporin A may be administered by injection and the non-specific suppressor cell inducing compound may be administered orally.

The therapeutic efficacy of a pharmaceutical composition of the invention was tested according to the procedure of Kupiec-Weglinski, J. W., et al., (1988) *Transplant Proc.* 2:207–216 (hereinafter "Kupiec-Weglinski") to determine its in vivo potency as an acute transplantation/graft rejection modulator.

Briefly, to preform these experiments, the following protocol was employed. Male inbred adult rats (Lewis-Brown Norway F1 Hybrid rats, obtained from Harlan sprague-Dawley Inc., Indianapolis, Ind.) were used. Lewis-Brown Norway F1 Hybrid cardiac allografts were transplanted to the abdominal great vessels of Lewis recipients. The animals were administered compounds according to the following five distinct regimens.

Protocol I. Pretreatment Protocol—20 mg/kg/day of Compound A was administered orally for 7 consecutive days prior to transplantation (days −7 to −1).

Protocol II Treatment Protocol—20 mg/kg/day of Compound A was administered orally for 7 consecutive post-transplant days (days 0–6) followed by intermittent 5 day courses (days 9–13 and 16–20).

Protocol III Pretreatment and Treatment Protocol—20 mg/kg/day of Compound A was administered orally for 7 consecutive days prior to transplantation (days −7 to −1) followed by intermittent 5 day courses (days 9–13 and 16–20).

Protocol IV Combination Protocol—20 mg/kg/day of Compound A was administered orally and 1.5 mg/kg/day of cyclosporin A was administered by injection for 7 consecutive post-transplant days (days 0–6).

Protocol V Untreated.

Ventricular contractions were assessed daily by palpation through the recipient flank. Rejection was defined as the day of cessation of myocardial contractions and confirmed histologically.

In the rats treated with a single compound (i.e., pretreatment protocol, treatment protocol or pretreatment and treatment protocol), the graft survival time was increased from an average of 7 days in the untreated model to an average of 16 days using Compound A. Cyclosporin A, at a dose of 1.5 mg/kg/day, when used alone in this model increased the graft survival time from an average of 7 days in the untreated model to an average of 12 days. (See, Kupiec-Weglinski). Alternatively, in the rats treated with the combination protocol, the transplants were routinely retained for over 40 days. To increase the graft survival time to equal that of the Combination Protocol using cyclosporin A alone requires a dosage an order of magnitude higher than that used in the combination protocol, i.e., 15 mg/kg/day (See, Kupiec-Weglinski). Thus, the administration of the claimed pharmaceutical composition was synergistic, i.e., it extended the graft survival time significantly longer than can be obtained by either compound alone or the additive survival time (28 days), and reduced the efficacious dosage of cyclosporin A by one order of magnitude. Since cyclosporin A is known to be highly nephrotoxic, and the level of nephrotoxicity increases with increasing dosages, reducing the dosage cyclosporin A required to obtain the desired immunosuppressive effect is highly desirable. Thus, it is expected that the discovery that the compositions and method of this invention are synergistic will enable the treatment of disorders requiring immunosuppression with the efficacy of conventional treatment methods but with lower toxicity problems. The results of the above experiment are summarized in the following Table 1.

TABLE 1

Effects of Various Treatment Protocols with Compound A on Lewis Rat Recipients of Lewis-Brown Norway F1 hybrid Cardiac Allografts.

|  | N | GRAFT SURVIVAL (days) | MEAN ± SD |
|---|---|---|---|
| Protocol I | 7 | 10,11,12,13,14,16,27 | 14.7 ± 5.8 |
| Protocol II | 7 | 14,16,16,16*,16*,19,20 | 16.7 ± 2.0 |
| Protocol III | 7 | 8,15,16,16,16,19,22, | 16.0 ± 4.3 |
| Protocol IV | 3 | 42,42,indefinite survival | |
| Protocol V (Untreated) | 7 | 6,7,7,7,8,8,8 | 7.3 ± 0.8 |

N is the number of rats tested
*graft survival in hosts treated for 7 post-transplant days only The data in the above Table 1 clearly demonstrates the synergistic effects of a combination of cyclosporin A and a non-specific suppressor cell inducing compound on the rejection of cardiac allografts in adult male rats.

The claimed pharmaceutical compositions are incorporated into convenient dosage forms such as capsules, tablets, or injectable preparations. Solid or liquid pharmaceutical carriers are employed. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

The pharmacokinetic properties of each active component of the pharmaceutical composition of the invention must be contemplated when formulating conventional dosage regimens. Both components can be incorporated into a timed release dosage unit form in which several doses are treated for delayed or sustained release of the medicament. Such dosage units may comprise sustained release granules, sugar centered spheres or multilayered tablets in each of which the availability of the active ingredient is controlled by coating with a lupid or polymeric material.

The claimed pharmaceutical composition and method are useful in effecting immunosuppression in mammals. Thus, they have therapeutic and/or prophylactic utility in treating diseases and conditions wherein inducing an immune suppression response is desired. Such diseases and conditions include, but are not limited to, Rheumatiod arthritis, systemic lupus erythematosis, multiple sclerosis, acute transplantation/graft rejection, myasthenia gravis, progressive systemic sclerosis, multiple myeloma, atopic dermatitis, hyperimmunoglobin E, hepatitis B antigen negative chronic active hepatitis, Hashimoto's thyroiditis, Familial Mediterranean fever, Grave's disease, autoimmune hemolytic anemia, primary biliary cirrhosis and inflammatory bowel disease.

This invention also relates to a method of inducing an immunosuppressive effect in a mammal, including a human, in need thereof which comprises administering a non-specific suppressor cell inducing compound and Cyclosporin A to such mammal. Both prophylactic and therapeutic induction are contemplated. One of skill in the art will recognize that the exact dosage and treatment regimen to be utilized in any particular situation will necessarily depend on the exact disease state to be treated, the age, weight sex and health of the particular animal being treated and that such optimums can be determined by conventional techniques.

To maximize its synergistic effect, the individual compounds of the claimed combinations can be administered as a single pharmaceutical composition or consecutively in separate pharmaceutical compositions, whichever administration scheme may be appropriate. One of skill in the art using conventional techniques can determine the most appropriate way to administer the two compounds (consecutively versus simultaneously) depending on such factors as the age, sex weight and health of the patient and the disease state to be treated.

The dose of the non-specific suppressor cell inducing compounds to be used in the method of the invention is selected from the range of about 0.01–10 mg/kg of body weight per day, preferably about 0.1–1 mg/kg. The dose of Cyclosporin A to be used in the method of the invention is selected from the range of 0.1 mg/kg–20 mg/kg of body weight per day, preferably 0.1 mg/kg–2.0 mg/kg.

The selected dose is administered to a mammal in need of immounosuppression from 1–6 times daily, and is administered topically, orally, rectally, by injection, or continuously by infusion. The administration route which is most appropriate is readily determined by one of skill in the art using conventional techniques. Oral dosage units for human administration preferably contain from 0.1 to 500 mg of each active compound. Oral administration, which uses lower dosages is preferred. Parenteral administration, at higher dosages, however, also can be used when safe and convenient for the patient.

The following examples illustrate preparation of the claimed pharmaceutical compositions. The examples are not intended to limit the scope of the invention as defined hereinabove and as claimed below.

EXAMPLE 1

Gelatin Capsule

An oral dosage form for administering the claimed compounds and compositions is produced by screening, mixing and filling into hard gelatin capsules the ingredients in the proportions shown in Table II below.

TABLE II

| Ingredients | Amounts |
|---|---|
| N,N-dimethyl-8,8-dipropyl-2-azaspiro[4,5]decane-2-propanamine | 10 mg |
| Cylcopsorin A | 100 mg |
| Magnesium stearate | 2 mg |
| Lactose | 30 mg |
| Starch | 10 mg |

EXAMPLE 2

Tablet

The microcrystalline cellulose, lactose and claimed compounds and compositions shown in Table III below, are mixed and granulated in the proportions shown with a 10% gelatin solution. The wet granules are screened, dried, mixed with the starch, talc and stearic acid, screened and compressed into a tablet.

TABLE III

| Ingredients | Amounts |
| --- | --- |
| N,N-dimethyl-8,8-dipropyl-2 azaspiro[4,5]decane-2-propanamine | 10 mg |
| Cyclosporine A | 100 mg |
| Microcrystalline cellulose | 30 mg |
| Lactose | 30 mg |
| Starch | 10 mg |
| Talc | 4 mg |
| Stearic acid | 4 mg |

EXAMPLE 3

Injectable Preparation

Cyclospirin A and N,N-dimethyl-8,8-dipropyl-2-azaspiro[4,5]decane-2-propanamine are solubilized or dispersed in oil based systems shown below to prepare an injectable formulation:

| Ingredients | Amounts |
| --- | --- |
| N,N-dimethyl-8,8-dipropyl-2-azaspiro[4,5]decane-2-propanamine | 10 mg |
| Cyclosporine A | 100 mg |
| Polyoxyethylated Castor Oil or Arachis Oil | 13 mg |
| Alcohol | 33% v/v |
| Sterile Water for Injection | 1 ml |

EXAMPLE 4

The following compounds (expressed as base weight) are mixed together with 30 mg of lactose and 2 mg of magnesium stearate and 10 mg starch then filled into a hard gelatin capsule. These capsules are administered from 1–6 times daily to a patient in need of immunosuppressive activity.
A. N,N-dimethyl-8,8-dipropyl-2-azaspiro[4,5]decane-2-propanamine 10 mg; cyclosporin A 100 mg ps B. N,N-diethyl-8,8-dipropyl-2-azaspiro[4,5]decane-2-propanamine 10 mg; cyclosporin A 100 mg
C.

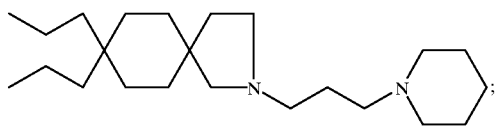

10 mg; cyclosporin A 100 mg

EXAMPLE 5

Soft Gelatin Capsule

An oral dosage form for administering the claimed compounds and compositions is produced by dispersing claimed compounds in polyethylene glycol vegetable oil and filling into soft gelatin capsules:

| Ingredients | Amounts |
| --- | --- |
| N,N-dimethyl-8,8-dipropyl-2-azaspiro[4, 5]decane-2-propanamine | 10 mg |
| Cyclosporin A | 100 mg |
| Polyehtylene Glycol | 50 mg |
| Vegetable Oil | 50 mg |

EXAMPLE 6

Micorparticulate System

The microcyrstalline cellulose, starch, and claimed compounds listed below are screened, mixed and spheronized in the proportions shown with a 10% gelatin solution. The wet particles are screened, dried, and sized. The resulting dried particles can be film-coated and filled into a hard gelatin capsule or compressed into a tablet with the addition of magnesium stearate.

| Ingredients | Amounts |
| --- | --- |
| N,N-dimethyl-8,8-dipropyl-2 azaspiro[4,5]decane-2-propanamine | 10 mg |
| Cyclosporin A | 100 mg |
| Microcrystalline Cellulose | 50 mg |
| Starch | 10 mg |
| Magnesium Stearate | 2 mg |

EXAMPLE 7

Oral Solution

An oral solution dosage form for administering the claimed compounds and compositions is produced by dissolving claimed compounds in propylene glycol and mixing with remaining ingredients in the following proportions shown below:

| Ingredients | Amounts |
| --- | --- |
| N,N-dimethyl-8,8-dipropyl-2-azaspiro[4, 5]decane-2-propanamine | 10 mg |
| Cyclosporin A | 100 mg |
| Sorbitol Solution | 10 mg |
| Propylene Glycol | 40 mg |
| Purified Water | 40 mg |

EXAMPLE 8

Oral Emulsion

An oral emulsion dosage form for administering the claimed compounds and compositions is produced by dissolving claimed compounds in vegetable oil. The polyoxyethylene sorbitan ester and sorgbitol solution are dissolved in water, and the oil mixture is dispersed in the water mixture forming an oil-in-water emulsion.

| Ingredients | Amounts |
| --- | --- |
| N,N-dimethyl-8,8-dipropyl-2-azaspiro[4, 5]decane-2-propamine | 10 mg |
| Cyclosporin A | 100 mg |
| Vegetable Oil | 50 mg |
| Polyoxyethylene Sorbitan Ester | 20 mg |
| Sorbitol Solution | 10 mg |
| Purified Water | 100 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A method of inducing immunosuppression in a mammal, including a human, in need thereof which comprises the coadministration of a non-specific suppressor cell inducing compound comprises N,N-dimethyl-8,8-dipropyl-2-azaspiro[4,5]decane-2-propanamine or a pharmaceutically acceptable salt thereof in combination with cyclosporin A in such amounts so as to provide a synergistic immunosuppressive effect.

2. The method of claim 1 in which immunosuppression is being induced in an animal suffering from acute transplantation/graft rejection.

3. The method of claim 1 in which immunosuppression is being induced in an animal suffering from
Rheumatoid arthritis,
systemic lupus erythermatosis,
multiple sclerosis,
myasthenia gravis,
progressive systemic sclerosis,
multiple myeloma,
atopic dermatitis,
hyperimmunoglobin E,
hepatitis B antigen negative chronic active hepatitis,
Hashimoto's thyroiditis,
Familial Mediterranean fever,
Grave's disease,
autoimmune hemolytic anemia,
primary biliary cirrhosis
insulin dependent diabetes mellitus or
inflammatory bowel disease.

4. A method of claim 1 in which the non-specific suppressor cell inducing compound and cyclosporin A are administered simultaneously.

5. The method of claim 1 in which the non-specific suppressor cell inducing compound and cyclosporin A are administered consecutively.

* * * * *